(12) United States Patent
Umebayashi

(10) Patent No.: US 10,238,549 B2
(45) Date of Patent: Mar. 26, 2019

(54) METHOD FOR PRODUCING DISPOSABLE WORN ARTICLE

(71) Applicant: ZUIKO CORPORATION, Osaka (JP)

(72) Inventor: Toyoshi Umebayashi, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 372 days.

(21) Appl. No.: 15/310,178

(22) PCT Filed: Jun. 25, 2015

(86) PCT No.: PCT/JP2015/068376
§ 371 (c)(1),
(2) Date: Nov. 10, 2016

(87) PCT Pub. No.: WO2015/199186
PCT Pub. Date: Dec. 30, 2015

(65) Prior Publication Data
US 2017/0156936 A1    Jun. 8, 2017

(30) Foreign Application Priority Data

Jun. 26, 2014  (JP) ................. 2014-131083

(51) Int. Cl.
*A61F 13/15*   (2006.01)
*A61F 13/49*   (2006.01)
(Continued)

(52) U.S. Cl.
CPC ........ *A61F 13/15* (2013.01); *A61F 13/15577* (2013.01); *A61F 13/15593* (2013.01);
(Continued)

(58) Field of Classification Search
CPC .......... A61F 13/49011; A61F 13/49012; A61F 13/49061; A61F 13/15699;
(Continued)

(56) References Cited

U.S. PATENT DOCUMENTS

2006/0151093 A1*  7/2006  Nakakado ......... A61F 13/15593
                                                                156/164
2006/0254708 A1   11/2006  Wada et al.
(Continued)

FOREIGN PATENT DOCUMENTS

JP   H04-144558 A    5/1992
JP   2007-181543 A   7/2007
(Continued)

OTHER PUBLICATIONS

International Search Report Issued in PCT/JP2015/068376 dated Sep. 15, 2015.

*Primary Examiner* — Scott W Dodds
(74) *Attorney, Agent, or Firm* — Renner, Otto, Boisselle and Sklar, LLP

(57) ABSTRACT

A method including: placing at least one elastic member stretchable in the carrying direction so that at least one elastic member extends in base portions of each continuous portion located at the same positions in the carrying direction as protruding portions or in the protruding portions; and intermittently folding the divided non-woven fabrics so that the elastic member is sandwiched between the base portions and the protruding portions and so that layered portions are formed, each layered portion including a protruding portion laid on a base portion adjacent to the protruding portion.

7 Claims, 15 Drawing Sheets

(51) Int. Cl.
*A61F 13/511* (2006.01)
*B32B 5/02* (2006.01)
*A61F 13/496* (2006.01)

(52) U.S. Cl.
CPC .. *A61F 13/15699* (2013.01); *A61F 13/15747* (2013.01); *A61F 13/496* (2013.01); *A61F 13/49011* (2013.01); *A61F 13/49061* (2013.01); *A61F 13/511* (2013.01); *B32B 5/022* (2013.01)

(58) Field of Classification Search
CPC .. A61F 2013/49025; A61F 2013/49026; A61F 2013/49028
USPC .......................................................... 156/259
See application file for complete search history.

(56) References Cited

U.S. PATENT DOCUMENTS

| | | |
|---|---|---|
| 2012/0024452 A1 | 2/2012 | Sakaguchi et al. |
| 2013/0110073 A1 | 5/2013 | Umebayashi |

FOREIGN PATENT DOCUMENTS

| | | |
|---|---|---|
| JP | 2010-142616 A | 7/2010 |
| WO | WO 2005-013871 A1 | 2/2005 |
| WO | WO 2012-017817 A1 | 2/2012 |
| WO | WO 2013-080852 A1 | 6/2013 |

* cited by examiner

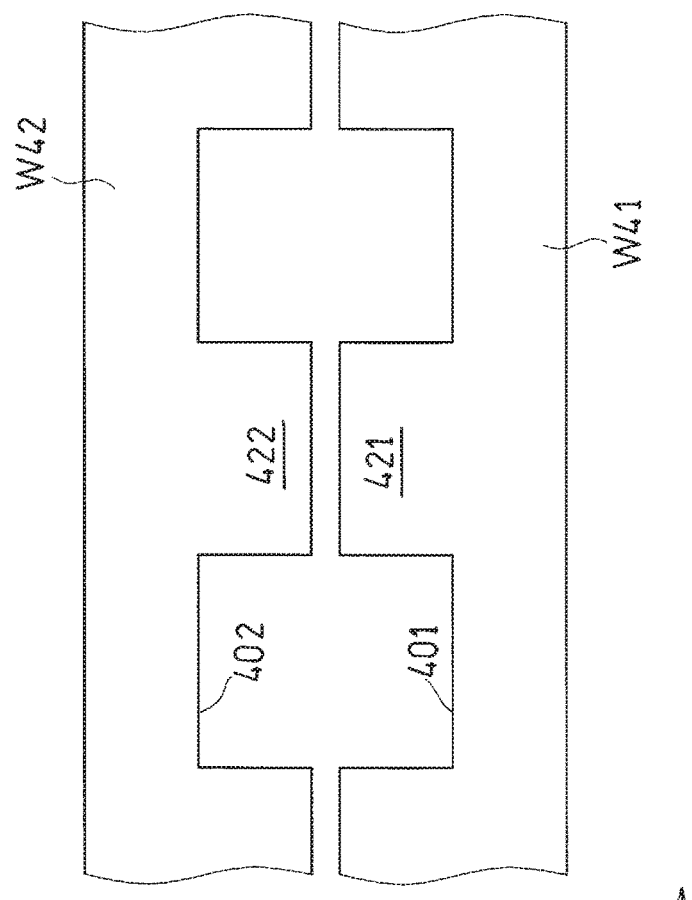
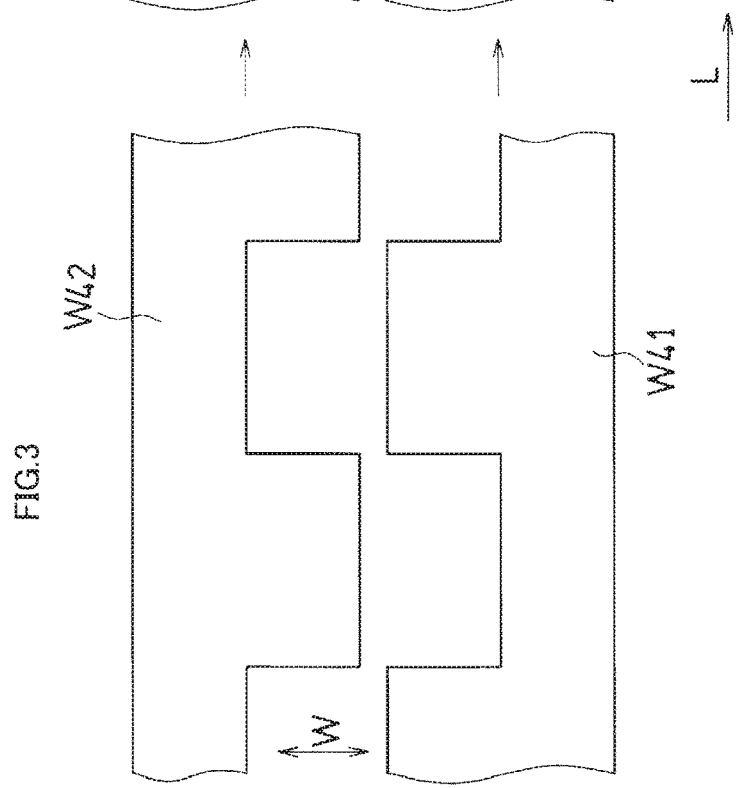
FIG.3

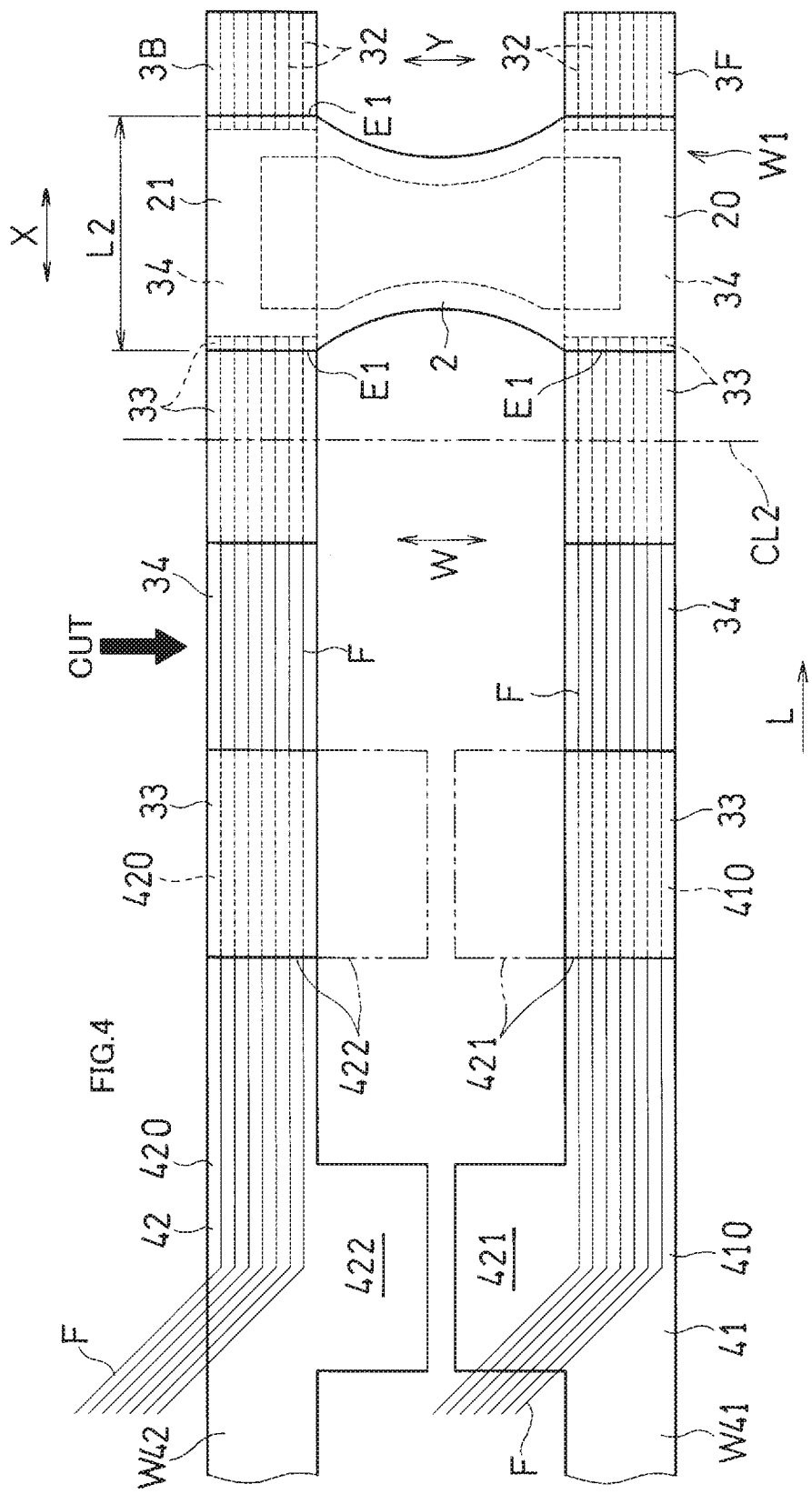

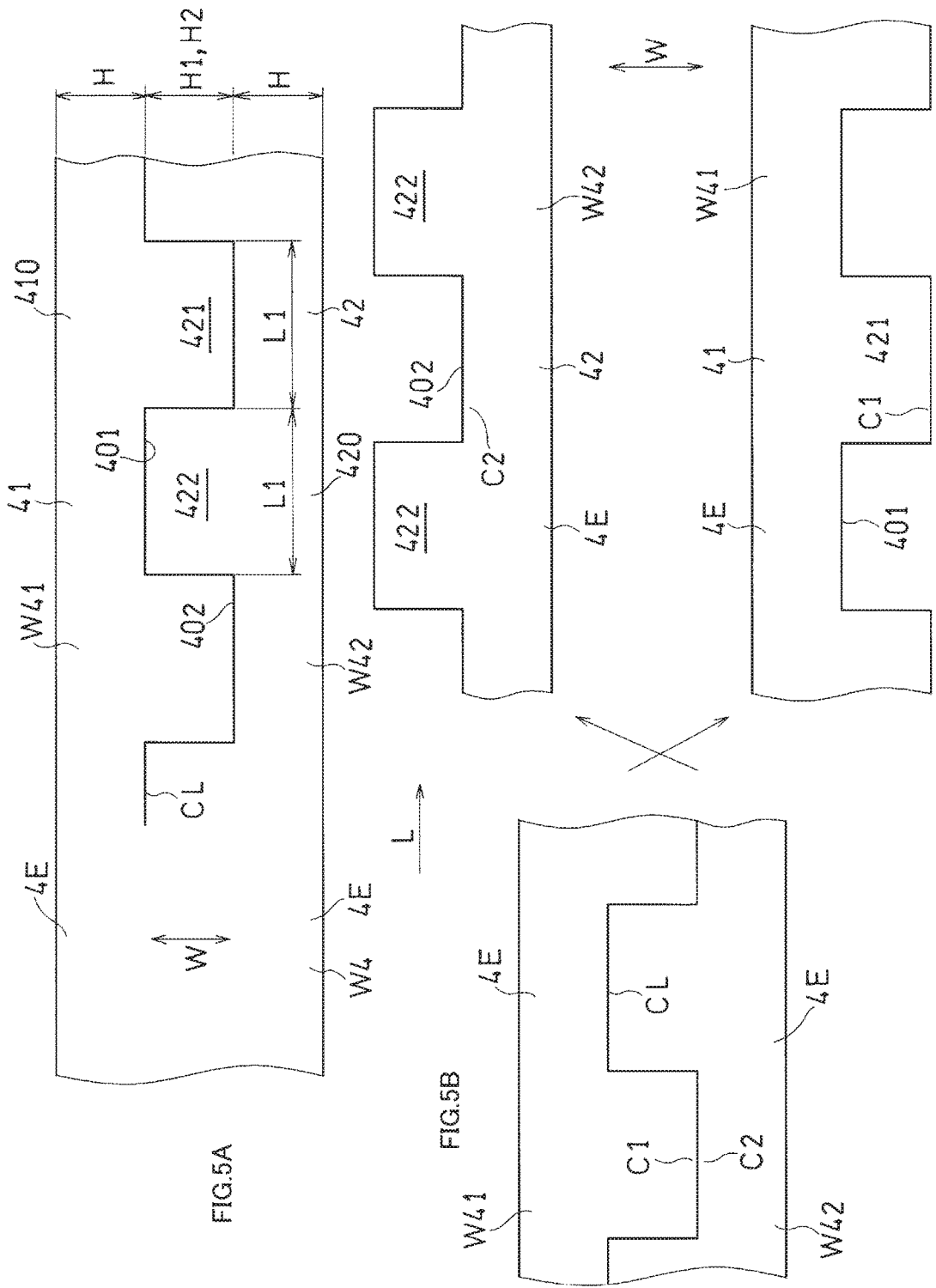

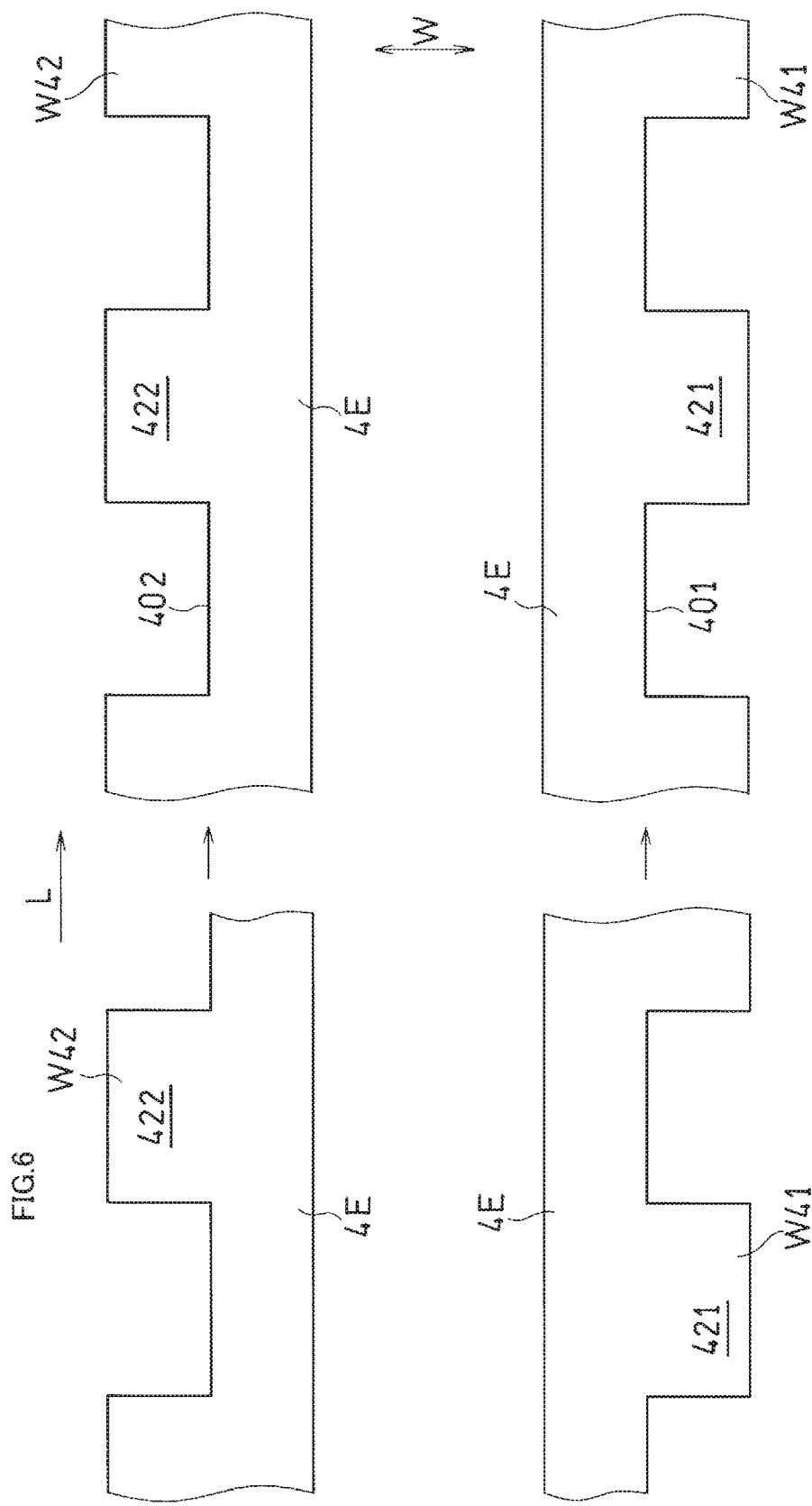

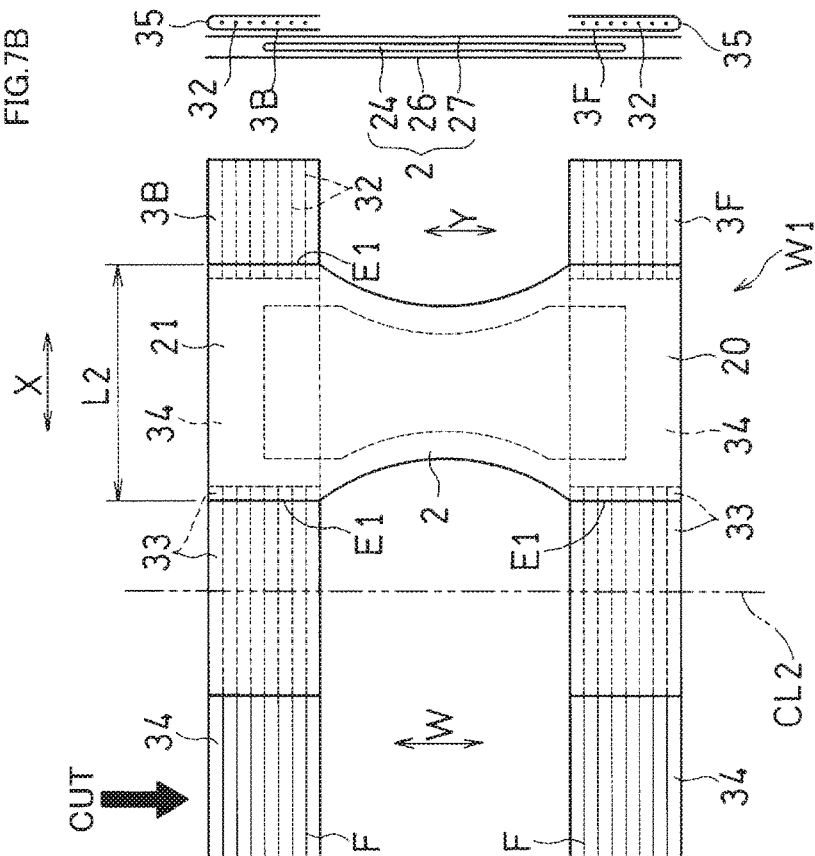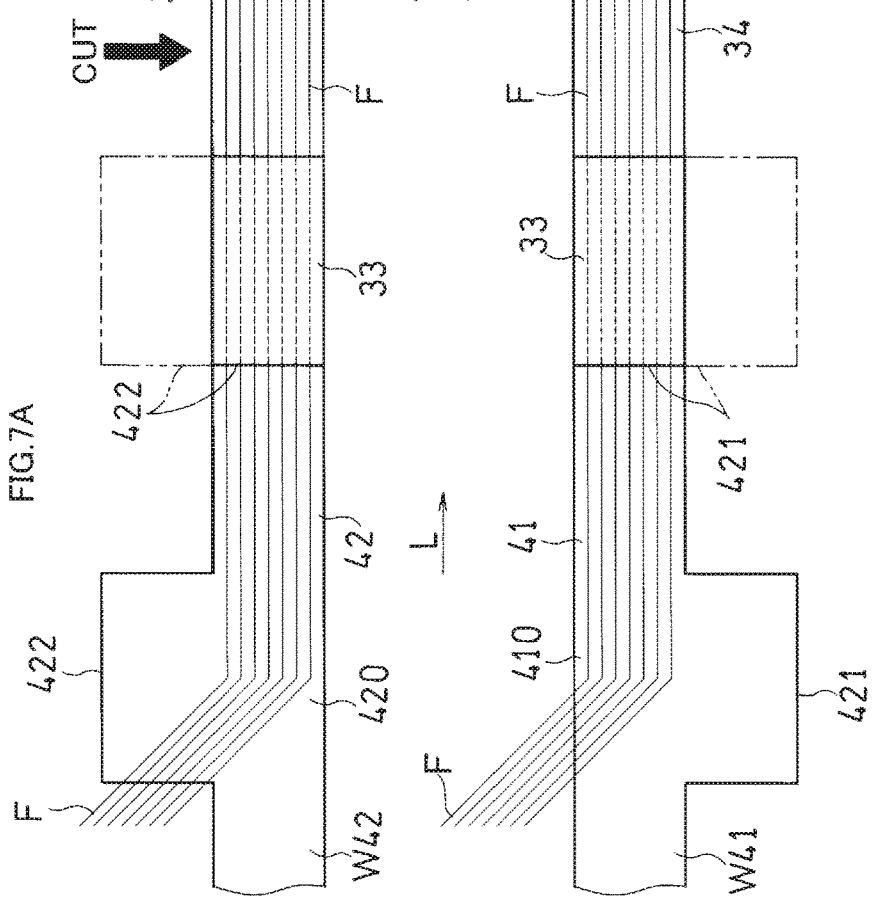

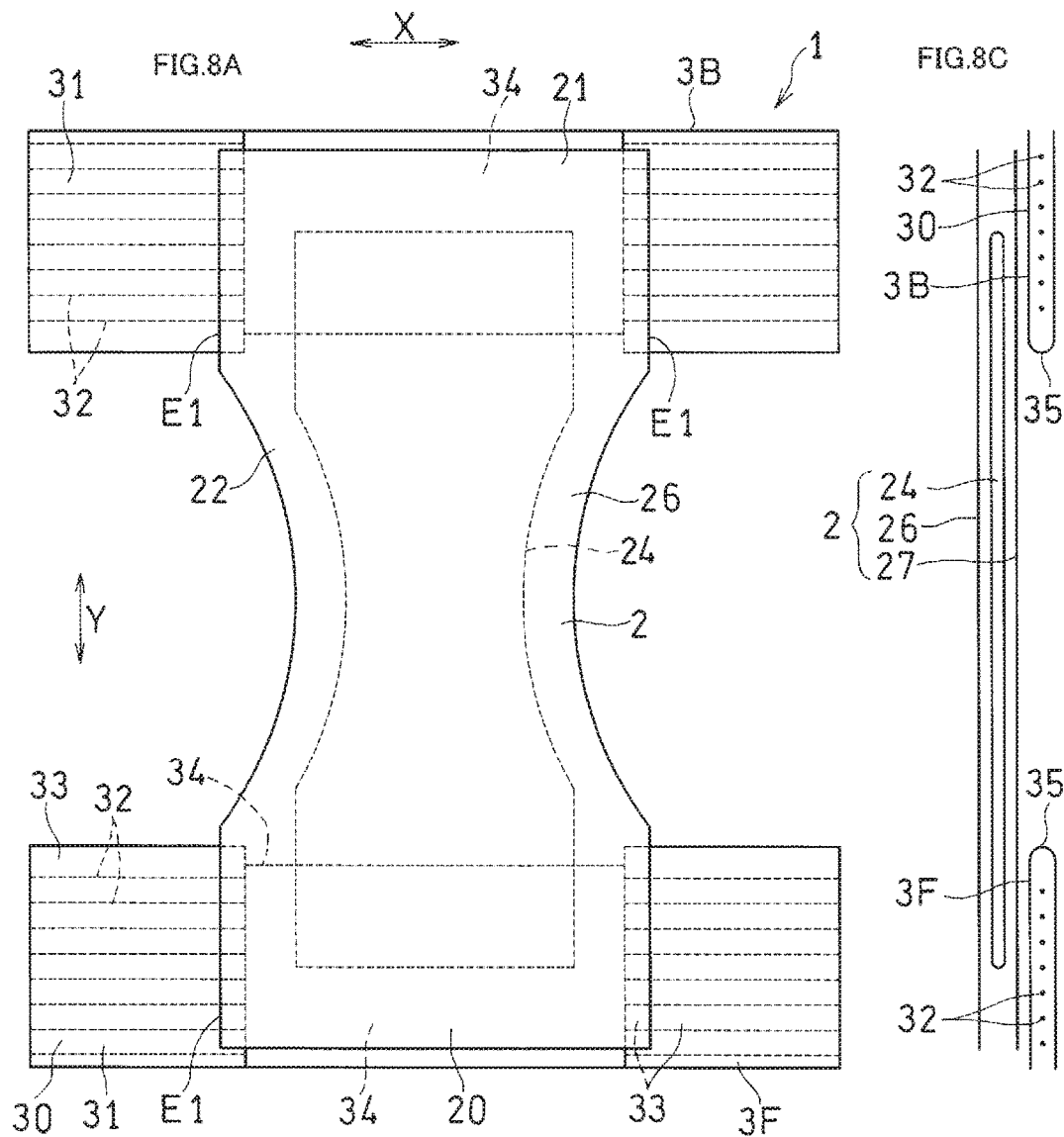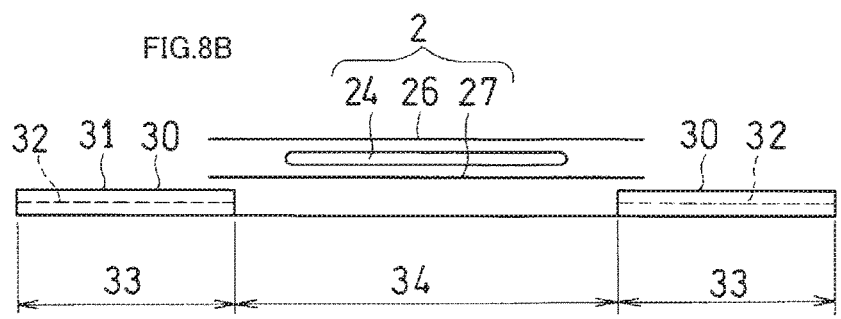

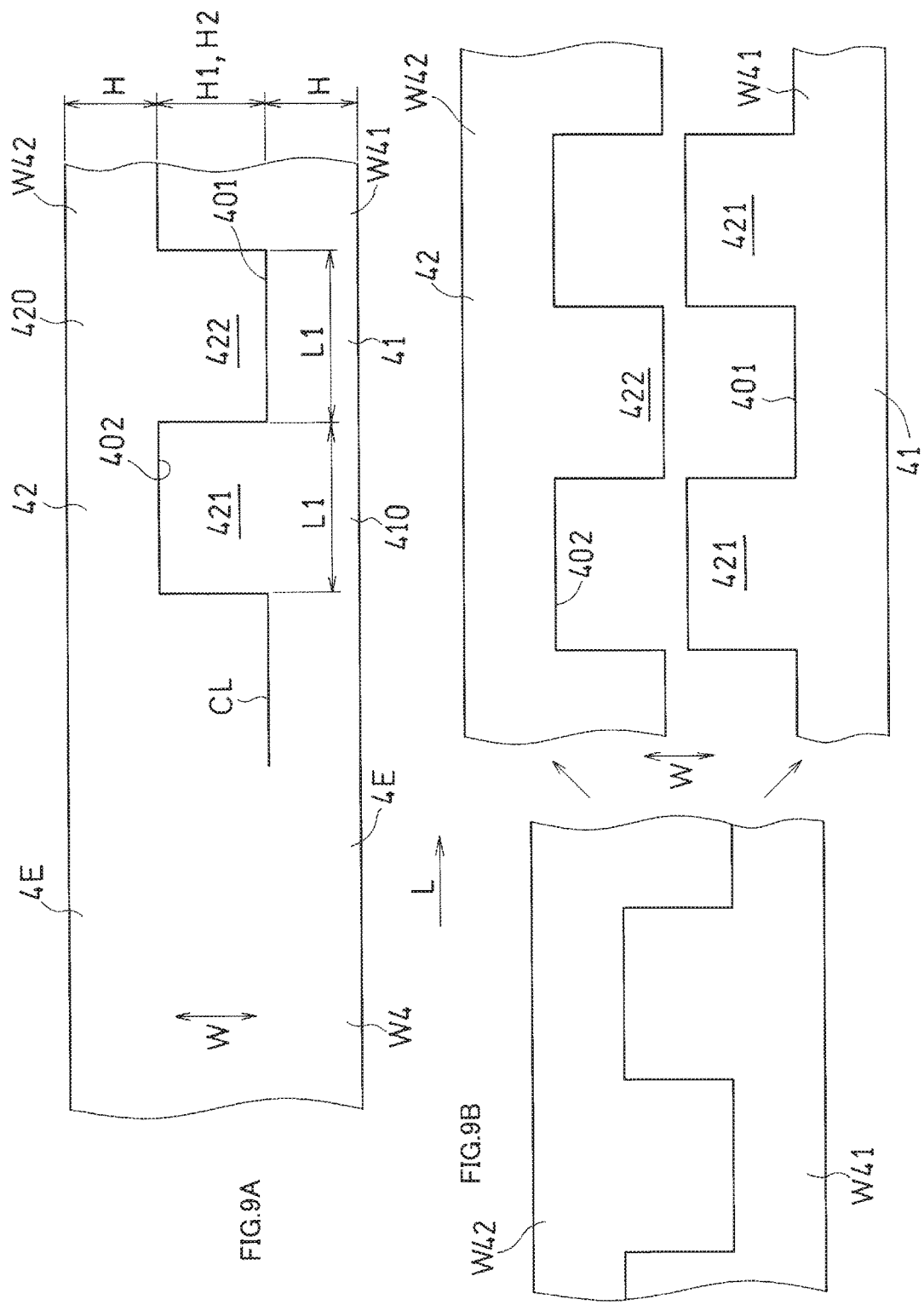

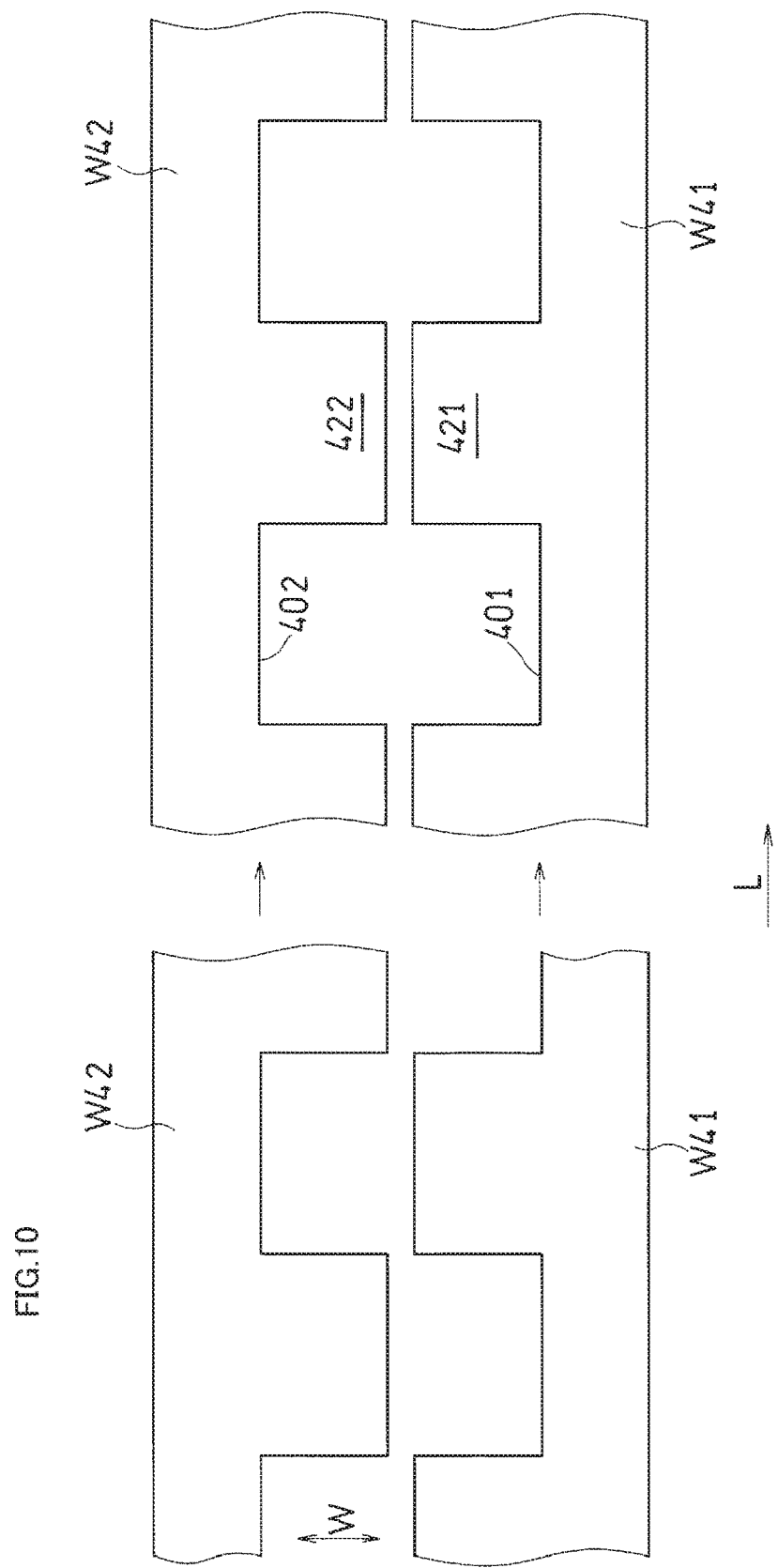

METHOD FOR PRODUCING DISPOSABLE WORN ARTICLE

TECHNICAL FIELD

The present invention relates to a method for producing a disposable worn article.

BACKGROUND ART

A method of sandwiching an elastic member between two sheets of non-woven fabric to produce an around-torso member extending in the girth direction is well known in the art. Moreover, a method of providing a pair of such around-torso members and providing an absorbent body so as to bridge between the around-torso members is also well known in the art.

CITATION LIST

Patent Literature

[First Patent Document] JP2007-181543A (front page)

SUMMARY OF INVENTION

With the conventional techniques, however, the two sheets of non-woven fabric are layered together across the entire length of the around-torso member in the girth direction. This results in a waste of non-woven fabric. Moreover, over the front torso and the rear torso, the two sheets of non-woven fabric or the laminate overlap the absorbent body, resulting in stiffness, thereby deteriorating the wearability (comfortable wearing).

It is an object of the present invention to provide a method for producing a disposable worn article, with which the material cost can be reduced and some improvement in wearability can be expected.

A production method of the present invention is a method for producing a disposable worn article comprising a pair of around-torso members covering a torso of a wearer and extending in a girth direction, and an absorbent body provided so as to bridge between the pair of around-torso members, extending in a longitudinal direction perpendicular to the girth direction, and covering a crotch of the wearer, the method including the steps of:

cutting a continuous non-woven fabric, which has a pair of side edge portions extending in a carrying direction, along a wave-shaped (corrugated) cutting (slitting, severing) line having a predetermined rectangular (rectangle-like, angular) shape while the continuous non-woven fabric is carried in the carrying direction so as to divide the continuous non-woven fabric into a first continuous divided non-woven fabric and a second continuous divided non-woven fabric, the first continuous divided non-woven fabric having first protruding (convex) portions protruding in a width direction perpendicular to the carrying direction from a first continuous portion continuous in the carrying direction, and the first continuous divided non-woven fabric forming one of the pair of around-torso members, the second continuous divided non-woven fabric having second protruding (convex) portions protruding in the width direction from a second continuous portion continuous in the carrying direction, and the second continuous divided non-woven fabric forming another (the other) one of the pair of around-torso members;

placing at least one elastic member stretchable in the carrying direction at least on the first and second protruding portions of the first and second divided non-woven fabrics, or on base portions of the first continuous portion located at the same positions in the carrying direction as the first protruding portions and on base portions of the second continuous portion located at the same positions in the carrying direction as the second protruding portions;

folding the first and second divided non-woven fabrics so that the elastic member is sandwiched between the base portions and the adjacent first protruding portions of the first divided non-woven fabric and between the base portions and the adjacent second protruding portions of the second divided non-woven fabric, and so that layered (superimposed, folded) portions are formed in the first and second divided non-woven fabrics, the layered portions of the first divided non-woven fabric including the first protruding portions laid on the base portions adjacent to the first protruding portions, and the layered portions of the second divided non-woven fabric including the second protruding portions laid on the base portions adjacent to the second protruding portions;

changing a positional relationship between the first and second divided non-woven fabrics so that positions of the base portions of the first continuous divided non-woven fabric in the carrying direction are aligned (in phase) with positions of the base portions of the second continuous divided non-woven fabric in the carrying direction; and after the changing step, placing the absorbent body so as to bridge between, and to overlap, a non-layered (non-folded) portion of the first continuous divided non-woven fabric and a non-layered (non-folded) portion of the second continuous divided non-woven fabric, the non-layered portion of the first divided non-woven fabric extending between two of the layered portions adjacent to each other in the carrying direction and the non-layered portion of the second divided non-woven fabric extending between two of the layered portions adjacent to each other in the carrying direction, while the first and second continuous divided non-woven fabrics are carried generally in parallel to each other in the carrying direction, thereby producing a continuous laminate.

According to the present invention, on each divided non-woven fabric, layered portions, where an elastic member is sandwiched between two sheets (folded sheet) of non-woven fabric, are provided intermittently in the longitudinal direction, and non-layered portions, where the two sheets of non-woven fabric are not layered together (i.e., a non-woven fabric is not folded), are formed between layered portions. Therefore, there is unlikely a waste of non-woven fabric, and it is possible to reduce the material cost.

On the other hand, the end portions of the absorbent body in the longitudinal direction overlap thin non-layered portions, where the non-woven fabric is not layered (folded). That is, one end portion of the absorbent body overlaps a non-layered portion of the first divided non-woven fabric, and the other end portion of the absorbent body overlaps a non-layered portion of the second divided non-woven fabric. Therefore, the wearability will not be deteriorated by stiffness.

BRIEF DESCRIPTION OF DRAWINGS

FIG. 3 is a schematic plan view showing the changing step according to Embodiment 1 of the method of the present invention.

FIG. 4 is a schematic plan view showing the folding step and the producing step according to Embodiment 1 of the method of the present invention.

FIG. 5A is a schematic plan view showing the dividing step according to Embodiment 2 of the method of the present invention, and FIG. 5B is a schematic plan view showing the first sub-step according to this embodiment.

FIG. 6 is a schematic plan view showing the second sub-step according to Embodiment 2 of the method of the present invention.

FIG. 7A is a schematic plan view showing the folding step and the producing step according to Embodiment 2 of the method of the present invention, and FIG. 7B is a schematic cross-sectional view showing the worn article.

FIG. 8A is a plan view showing another example of the worn article according to the method of the present invention, and FIG. 8B and FIG. 8C are cross-sectional views showing the other example.

FIG. 9A is a schematic plan view showing the dividing step according to Embodiment 3 of the method of the present invention, and FIG. 9B is a schematic plan view showing the changing step according to this embodiment.

FIG. 10 is a schematic plan view showing the changing step according to Embodiment 3 of the method of the present invention.

DESCRIPTION OF EMBODIMENTS

Figure 1:
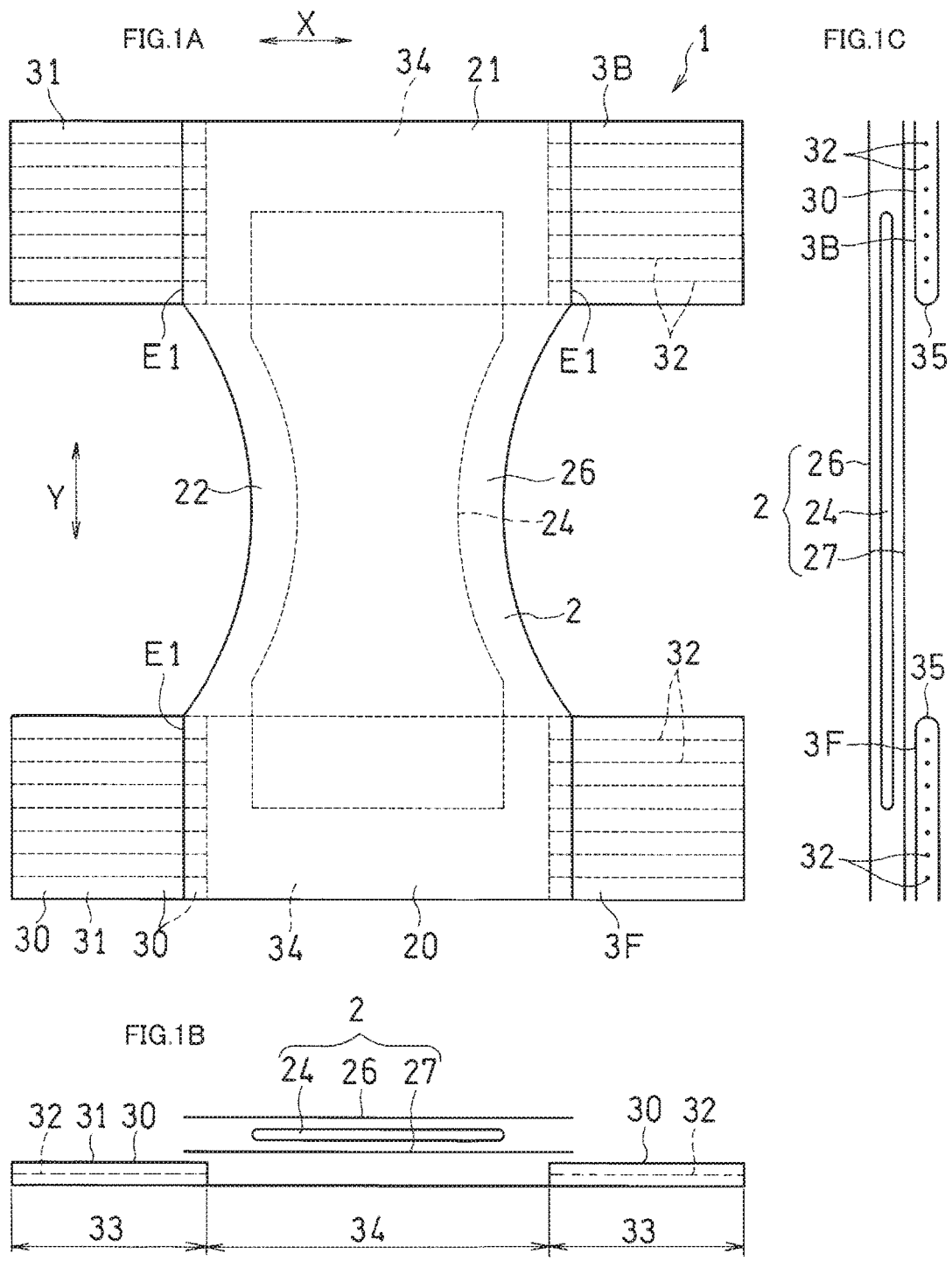
FIG. 1A is a plan view showing an example worn article according to the method of the present invention.
FIG. 1B and FIG. 1C are cross-sectional views showing the example.
Figure 2:
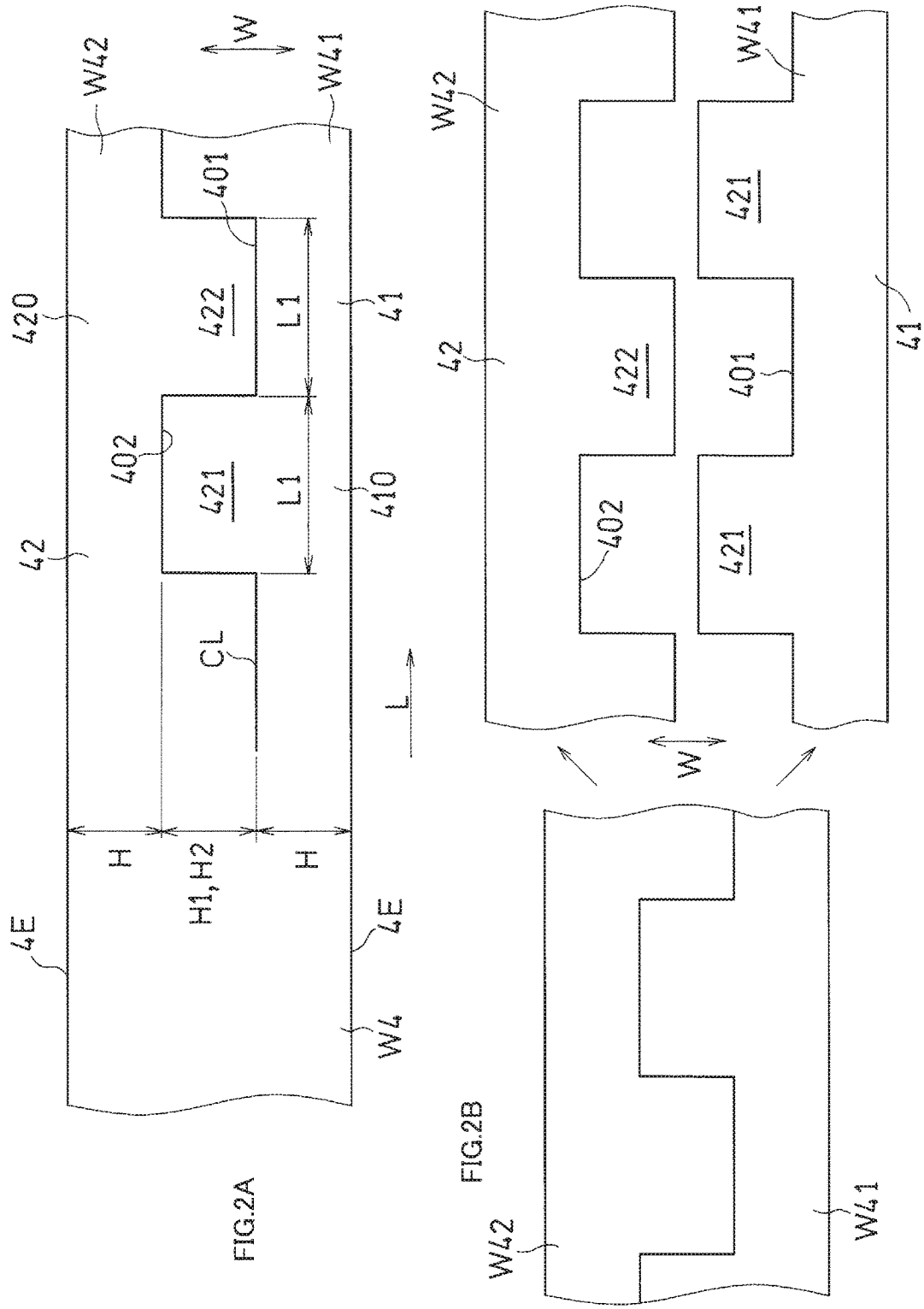
FIG. 2A is a schematic plan view showing the dividing step according to Embodiment 1 of the method of the present invention.
FIG. 2B is a schematic plan view showing the changing step according to this embodiment.

Preferably, the absorbent body includes torso portions each covering a front torso or a rear torso of the wearer; and the step of producing the continuous laminate is performed by placing the absorbent body so that two edge portions, in the girth direction, of the torso portion covering the front torso and two edge portions, in the girth direction, of the torso portion covering the rear torso respectively overlap portions of two of the layered portions of the first divided non-woven fabric adjacent to each other in the carrying direction and portions of two of the layered portions of the second divided non-woven fabric adjacent to each other in the carrying direction.

In this case, the edge portions of each torso portion of the absorbent body overlap portions of the layered portion. That is, for the first divided non-woven fabric, one edge portion in the girth direction of the torso portion covering the front torso or the rear torso overlaps a portion of one layered portion, and the other edge portion in the girth direction of the torso portion overlaps a portion of another layered portion adjacent to the aforementioned one layered portion in the carrying direction. For the second divided non-woven fabric, one edge portion in the girth direction of the torso portion covering the rear torso or the front torso overlaps a portion of one layered portion, and the other edge portion in the girth direction of the torso portion overlaps a portion of another layered portion adjacent to the aforementioned one layered portion in the carrying direction.

Therefore, the non-layered portion, which is less stiff (less rigid), of the around-torso member extending in the girth direction is reinforced by the absorbent body, and the layered portions are continuous with the reinforced non-layered portion. Therefore, the around-torso member is formed continuously in the girth direction by elements having an adequate rigidity.

Preferably, the dividing step is performed so that a dimension of each of the first protruding portions in the width direction is greater than a dimension of the continuous portion of the first continuous divided non-woven fabric in the width direction and so that a dimension of each of the second protruding portions in the width direction is greater than a dimension of the continuous portion of the second continuous divided non-woven fabric in the width direction.

In this case, the wide protruding portions will be easy to fold.

Preferably, the present production method further includes the step of folding back the side edge portions of the first and second divided non-woven fabrics continuously in the carrying direction so that skin-contact surfaces of end portions of the absorbent body in the longitudinal direction are covered by the side edge portions.

In this case, the folded-back side edge portions of the first and second continuous divided non-woven fabrics cover a portion of the end portions of the absorbent body in the longitudinal direction. Therefore, it is possible to prevent the end portions of the absorbent body from getting caught on toes of the wearer when wearing.

Preferably, in the present production method, the at least one elastic member includes a plurality of elastic members parallel to each other;

the placement step is performed by placing the plurality of elastic members so that the elastic members extend in parallel to each other and continuously in the carrying direction on the first and second continuous portions; and the method further comprises the step of nullifying tension of some or all of the plurality of elastic members in the non-layered portions of the first and second divided non-woven fabrics so that a shrinking (shrinkage) force of the elastic members is not exerted in the non-layered portions.

In this case, in the non-layered portions, some or all of the plurality of elastic members are nullified (made ineffective) to lose the shrinking force thereof. This will improve the feel and the wearability.

Preferably, the step of changing the positional relationship is performed by changing the positional relationship between the first continuous divided non-woven fabric and the second continuous divided non-woven fabric so that the first protruding portions and the second protruding portions oppose (face) each other.

In this case, the device for changing the arrangement will have a simple structure.

Preferably, the step of changing the positional relationship includes:

a first sub-step of changing the positional relationship between the first continuous divided non-woven fabric and the second continuous divided non-woven fabric in the width direction so that the pair of side edge portions are placed between a first severed edge of the first continuous divided non-woven fabric along the severing line and a second severed edge of the second continuous divided non-woven fabric along the severing line and so that the pair of side edges come closer to each other; and a second sub-step of changing the positional relationship between the first continuous divided non-woven fabric and the second continuous divided non-woven fabric in the carrying direction so that the first protruding portions and the second protruding portions are back to back with each other.

In this case, the upper ends of the flaps protruding in the girth direction from the absorbent body are folded back, which will improve the feel and handling.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

EMBODIMENTS

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

A structure of a worn article 1 according to Embodiment 1 of the present invention will now be described with reference to the drawings.

FIG. 1A to FIG. 4 show Embodiment 1.

As shown in FIG. 1A, the worn article 1 of Embodiment 1 has a left-right symmetric shape and structure, and includes an absorbent body 2, a front around-torso member 3F and a rear around-torso member 3B (a pair of around-torso members). The absorbent body 2 includes a front portion (torso portion) 20 covering the front torso of the wearer and extending in the girth direction X, a back portion (torso portion) 21 covering the rear torso of the wearer and extending in the girth direction X, and a crotch portion 22 covering the crotch between the front portion 20 and the back portion 21.

The crotch portion 22 is continuous with the front portion 20 and the back portion 21, and extends in the longitudinal direction Y perpendicular to the girth direction X. The absorbent body 2 forms a part or a whole of the crotch portion 22.

When worn, the crotch portion 22 is folded in two along a virtual line parallel to the girth direction X. Then, end portions in the girth direction X of the front around-torso member 3F and those of the rear around-torso member 3B are laid on each other.

As shown in FIG. 1A, the absorbent body 2 includes an absorbent core 24 indicated by a broken line, and the absorbent core 24 absorbs body fluid. As shown in FIG. 1B and FIG. 1C, the absorbent core 24 is sandwiched between a top sheet 26 and a back sheet 27, and the sheets 26 and 27 and the absorbent core 24 are layered together.

In FIG. 1B and FIG. 1C, the top sheet 26 is formed by a thin liquid-permeable non-woven fabric and covers the skin-contact surface of the absorbent core 24. A cuff (not shown) may be provided on the top sheet 26.

The back sheet 27 covers the non-skin-contact surface of the absorbent core 24 and is formed by a liquid-impermeable resin sheet. A design pattern, a graphical design and/or characters may be printed on the non-skin-contact surface of the back sheet 27 formed by a resin sheet. Alternatively, a sheet member with a design pattern, a graphical design and/or characters printed thereon may be attached to the non-skin-contact surface of the back sheet 27.

In FIG. 1A, the front around-torso member 3F is attached to the end portion of the front portion 20 of the absorbent body 2 in the longitudinal direction Y. On the other hand, the rear around-torso member 3B is attached to the end portion of the back portion 21 of the absorbent body 2 in the longitudinal direction Y.

The front and rear around-torso members 3F and 3B protrude from the absorbent body 2 in the girth direction X, and form a part of the front and rear around-torso portions. That is, as shown in FIG. 1A, the around-torso members 3F and 3B protrude in the girth direction X past the crotch portion 22, and extend in the girth direction X from the opposite edge portions (the end portions in the girth direction) E1 of the absorbent body 2.

The front and rear around-torso members 3F and 3B are formed by a non-woven fabric 30, which is partially layered, as shown in FIG. 1B and FIG. 1C, for example. That is, the around-torso members 3F and 3B are folded in two layered portions 33, each of which includes a flap 31 protruding in the girth direction X from the absorbent body 2 and the vicinity thereof. As shown in FIG. 1C, the around-torso members 3F and 3B are folded so that the bent portions 35 and 35 of the around-torso members 3F and 3B, which are folded in two, oppose each other.

For each of the around-torso members 3F and 3B, the non-woven fabric 30 is folded at positions separated from each other in the girth direction X, thereby forming the layered portions 33 and 883, as shown in FIG. 1B. A non-layered portion 34, where the non-woven fabric is not folded in two, is located between the layered portions 33 separated from each other in the girth direction X. Note that these non-woven fabrics 30 are breathable.

In FIG. 1A and FIG. 1B, most of the front portion 20 and most of the back portion 21 are laid on the non-layered portions 34, and two edge portions E1 of the front portion 20 in the girth direction X and those of the back portion 21 each overlap a portion of the layered portions 88.

In FIG. 1A, an elastic member 32 for fitting the worn article 1 to the wearer may be provided over the flaps 31 and the vicinity thereof (the layered portion 33), where the non-woven fabric 30 is folded in two. The elastic member 32 may be, for example, a plurality of rubber threads, rubber tapes, a material including at least one sheet of film or a thermoplastic resin, or the like. The elastic member 32 may be nullified (left with no shrinking force) in the center of the front portion and the back portion.

That is, the elastic member 32 may be nullified in the non-layered portions on which most of the end portion in the longitudinal direction Y of the front portion and most of the end portion in the longitudinal direction Y of the back portion are laid.

The absorbent body 2 may include around-leg portions necked (constricted, narrowed) in conformity with the legs of the wearer. In the around-leg portions or in areas continuous with the around-leg portions of the around-torso members 3F and 3B, another elastic member made of rubber threads may be provided, for example, so as to conform around the legs of the wearer.

Where the worn article is a diaper, male touch fasteners (not shown) may be secured to the skin-contact surface of flaps 31 of the rear around-torso member 3B, with female touch fasteners secured to the non-skin-contact surface of the front around-torso member 3F.

Note that a tape material with a fastening agent applied thereon may be used instead of the male touch fasteners, and in this case, the front around-torso member 3F, etc., needs to have a surface on which the fastening agent adheres easily.

Where the worn article is pants-shaped, the end portion in the girth direction X of the front around-torso member 3F and that of the rear around-torso member 3B may be welded together.

The absorbent body 2 is attached to the skin-contact surface of the around-torso members 3F and 3B.

In the present specification, the "skin-contact surface" refers to a surface that directly or indirectly faces the skin of the wearer when the worn article 1 is worn, and the "non-skin-contact surface" refers to the surface opposite to the skin-contact surface.

Next, a method for producing the present worn article 1 will be described with reference to FIG. 2A to FIG. 4.

As shown in FIG. 2A and FIG. 2B, a continuous non-woven fabric W4 having a pair of side edge portions 4E extending in the carrying direction L is carried in the carrying direction L. The continuous non-woven fabric W4 is slit along a rectangle-like wave-shaped severing line CL while being carried in the carrying direction L.

Thus, the continuous non-woven fabric W4 is divided into a first continuous divided non-woven fabric W41 having a first protruding portion 421 and a first depressed portion 401, and a second continuous divided non-woven fabric W42 having a second depressed portion 402 and a second protruding portion 422.

That is, the continuous non-woven fabric W4 is divided so that the first protruding portion 421 and the second protruding portion 422 are adjacent to each other in the carrying direction L.

The continuous divided non-woven fabrics W41 and W42 each form the around-torso member 3F or 3B.

The first protruding portion 421 protrudes from a first continuous portion 41, which is continuous in the carrying direction L, in the width direction W perpendicular to the carrying direction L. The second protruding portion 422 protrudes from a second continuous portion 42, which is continuous in the carrying direction L, in the width direction W.

Next, the first continuous divided non-woven fabric W41 and the second continuous divided non-woven fabric W42 of FIG. 2B are moved relative to each other in the width direction W so that the two continuous divided non-woven fabrics W41 and W42 are separated from each other in the width direction W perpendicular to the carrying direction L.

Then, the positional relationship in the carrying direction L between the first continuous divided non-woven fabric W41 and the second continuous divided non-woven fabric W42 is changed so that the first protruding portion 421 and the second protruding portion 422 of FIG. 3 oppose each other and the first depressed portion 401 and the second depressed portion 402 oppose each other. That is, the pair of continuous divided non-woven fabrics W41 and W42 are moved relative to each other in the carrying direction L by half the wavelength or by the (n+½) wavelength (n is a natural number) so that their protrusion/depression phases are matched with each other.

After or while changing the phase, the positional relationship between the first continuous divided non-woven fabric W41 and the second continuous divided non-woven fabric W42 in the width direction W is changed so that the first protruding portion 421 and the second protruding portion 422 come closer to each other.

After or before changing the arrangement, a plurality of threads of a continuous elastic member F are placed, in parallel to each other while being stretched in the carrying direction L, along the continuous portions 41 and 42 shown in FIG. 4. In this placement step, as will be described later, at least one elastic member that is stretchable in the carrying direction L may be placed intermittently so that the at least one elastic member extends at least in the base portions 410 and 420 located at the same positions in the carrying direction L as the protruding portions 421 and 422 of the continuous portions 41 and 42 or in the protruding portions 421 and 422.

The base portions 410 of the first divided non-woven fabric W41 are located intermittently in the carrying direction L, each base portion 410 being adjacent to a first protruding portion 421 in the width direction W. The base portions 420 of the second divided non-woven fabric W42 are located intermittently in the carrying direction L, each base portion 420 being adjacent to a second protruding portion 422 in the width direction W.

As indicated by phantom lines and solid lines in FIG. 4, the first protruding portions 421 of the first continuous divided non-woven fabric W41 are folded intermittently so that the continuous elastic member F is sandwiched between the base portion 410 and the first protruding portion 421 of the first divided non-woven fabric W41 and so that the first protruding portion 421 is laid on the base portion 410 that is adjacent to the first protruding portion 421, thereby forming the layered portion 33.

Simultaneously, the second protruding portions 422 of the second continuous divided non-woven fabric W42 are folded intermittently so that the continuous elastic member F is sandwiched between the base portion 420 and the second protruding portion 422 of the second divided non-woven fabric W42 and so that the second protruding portion 422 is laid on the base portion 420 that is adjacent to the second protruding portion 422, thereby forming the layered portion 33.

In the folding operation, the non-woven fabrics folded onto each other may be bonded or welded together with the continuous elastic member F sandwiched therebetween.

By successively performing the folding operation, the non-layered portions 34, where the protruding portions 421 and 422 are not layered, are formed intermittently along the continuous divided non-woven fabrics W41 and W42 between the layered portions 88. That is, on the continuous divided non-woven fabrics W41 and W42, the layered portions and the non-layered portions are formed alternately and repeatedly in the carrying direction L.

After forming the layered portions 33, a part or a whole of the continuous elastic member F is severed in the non-layered portions 34.

That is, as the continuous elastic member F in the non-layered portions 34 is severed, a part or a whole of the continuous elastic member F in the non-layered portions 34 is removed and the tension thereof is nullified. Note that the continuous elastic member F may snap back (contract, shrink) upon being severed. An adhesive may not be applied to the base portions 410 and 420 where the continuous elastic member F is severed.

After the severing, the absorbent body 2 is placed so as to bridge between, and to overlap, the non-layered portion 34 of the first continuous divided non-woven fabric W41 and the non-layered portion 34 of the second continuous divided non-woven fabric W42, while the first and second continuous divided non-woven fabric W41 and W42 are carried generally in parallel to each other in the carrying direction L, thereby producing the continuous laminate W1.

That is, the absorbent body 2 is placed on the first and second divided non-woven fabrics W41 and W42 so that one end portion of the absorbent body 2 in the longitudinal direction Y overlaps the non-layered portion 34 of the first divided non-woven fabric W41 and the other end portion of the absorbent body 2 overlaps the non-layered portion 34 of the second divided non-woven fabric W42.

In the step of producing the continuous laminate W1, the absorbent body 2 is placed so that two edge portions E1 of each of the torso portions 20 and 21 in the girth direction X overlap a portion of the layered portions 33.

That is, two edge portions E1 of the torso portion 20 (front portion) in the girth direction X overlap a portion of the layered portions 33 and 33 of the first divided non-woven fabric W41, which are adjacent to each other in the carrying direction L. On the other hand, two edge portions E1 of the torso portion 21 (back portion) in the girth direction X overlap a portion of the layered portions 33 and 33 of the second divided non-woven fabric W42, which are adjacent to each other in the carrying direction L.

As shown in FIG. 4, the continuous laminate W1 is cut along the virtual severing line CL2 indicated by a two-dot-chain line to a size (unit) of each individual worn article 1. That is, after the bridging, the around-torso members 3F and 3B are severed in the width direction W across the layered portions 33 of the first and second divided non-woven fabrics W41 and W42 to a length that corresponds to the individual worn article 1. Thus, the individual worn articles 1 shown in FIG. 1A to FIG. 1C are obtained.

Note that the continuous laminate W1 may be folded in two while in a continuous state before being cut into the individual worn articles 1. That is, the continuous laminate W1 may be folded in two so that the skin-contact surface of the first divided non-woven fabric W41 and the skin-contact surface of the second divided non-woven fabric W42 oppose each other.

Next, another embodiment will be described.

In the following embodiments, different structures and steps from those of Embodiment 1 will be described primarily and similar structures and steps to those of Embodiment 1 will not be described.

FIG. 5A to FIG. 7B show Embodiment 2.

In Embodiment 1 of FIG. 1C, the bent portions 35 of the around-torso members 3F and 3B are placed so as to be at the lower end of the around-torso members 3F and 8B when worn. In contrast, in this embodiment, the bent portion 35 of the around-torso members 3F and 3B are placed so as to be at the upper end of the worn article 1 when worn, as shown in the cross-sectional view of FIG. 7B.

In Embodiment 2, the step of changing the positional relationship between the first continuous divided non-woven fabric W41 and the second continuous divided non-woven fabric W42 of FIG. 5B includes the following first and second sub-steps.

In the first sub-step of FIG. 5B, the positional relationship between the first continuous divided non-woven fabric W41 and the second continuous divided non-woven fabric W42 in the width direction W is changed so that the pair of side edge portions 4E are placed between the first severed edge C1 of the first continuous divided non-woven fabric W41 along the severing line CL and the second severed edge C2 of the second continuous divided non-woven fabric W42 along the severing line CL and so that the pair of side edges 4E come closer to each other.

That is, the positional relationship between the first and second divided non-woven fabrics W41 and W42 is changed so that the first severed edge C1 and the second severed edge C2 are separated from each other in the width direction W and so that the pair of side edge portions 4E are placed between the first severed edge C1 and the second severed edge C2 separated from each other. The pair of side edge portions 4E are separated from each other while opposing each other in the width direction W.

In the second sub-step of FIG. 6, the positional relationship between the first continuous divided non-woven fabric W41 and the second continuous divided non-woven fabric W42 in the carrying direction L is changed so that the first protruding portion 421 and the second protruding portion 422 are back to back with each other.

That is, in the present production method, the positional relationship between the divided non-woven fabrics W41 and W42 can be changed so that the positions of the layered portions 33 of the first continuous divided non-woven fabric W41 in the carrying direction L of FIG. 7A are aligned with the positions of the layered portions 33 of the second continuous divided non-woven fabric W42 in the carrying direction L.

In other words, the positional relationship between the first and second divided non-woven fabrics W41 and W42 is changed so that the first base portion 410 adjacent to the first protruding portion 421 in the width direction W and the second base portion 420 adjacent to the second protruding portion 422 in the width direction W oppose each other in the width direction W.

FIG. 8A to FIG. 11 show Embodiment 3.

As shown in FIG. 8A, in this embodiment, the layered portion 33 is slightly protruding past (slightly larger than) the non-layered portion 34 toward the center in the longitudinal direction Y.

In this embodiment, the continuous non-woven fabric W4 is severed as shown in FIG. 9A and FIG. 9B.

That is, the dividing step is performed so that the dimension H1 of the first protruding portion 421 in the width direction W is greater than the dimension H of the continuous portion 41 of the first continuous divided non-woven fabric W41 in the width direction W and so that the dimension H2 of the second protruding portion 422 in the width direction W is greater than the dimension H of the continuous portion 42 of the second continuous divided non-woven fabric W42 in the width direction W.

Figure 11:
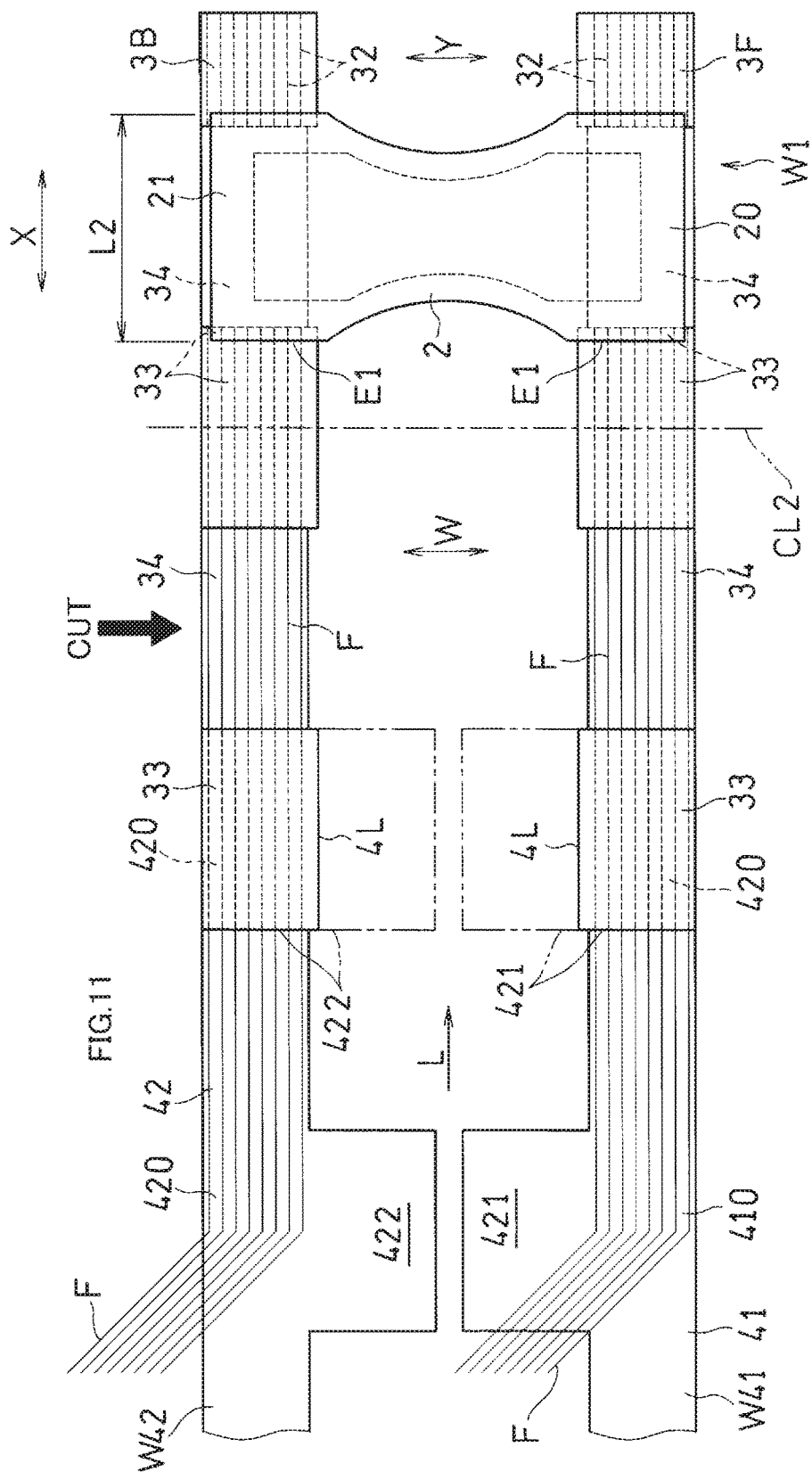
FIG. 11 is a schematic plan view showing the folding step and the producing step according to Embodiment 3 of the method of the present invention.
Figure 12:
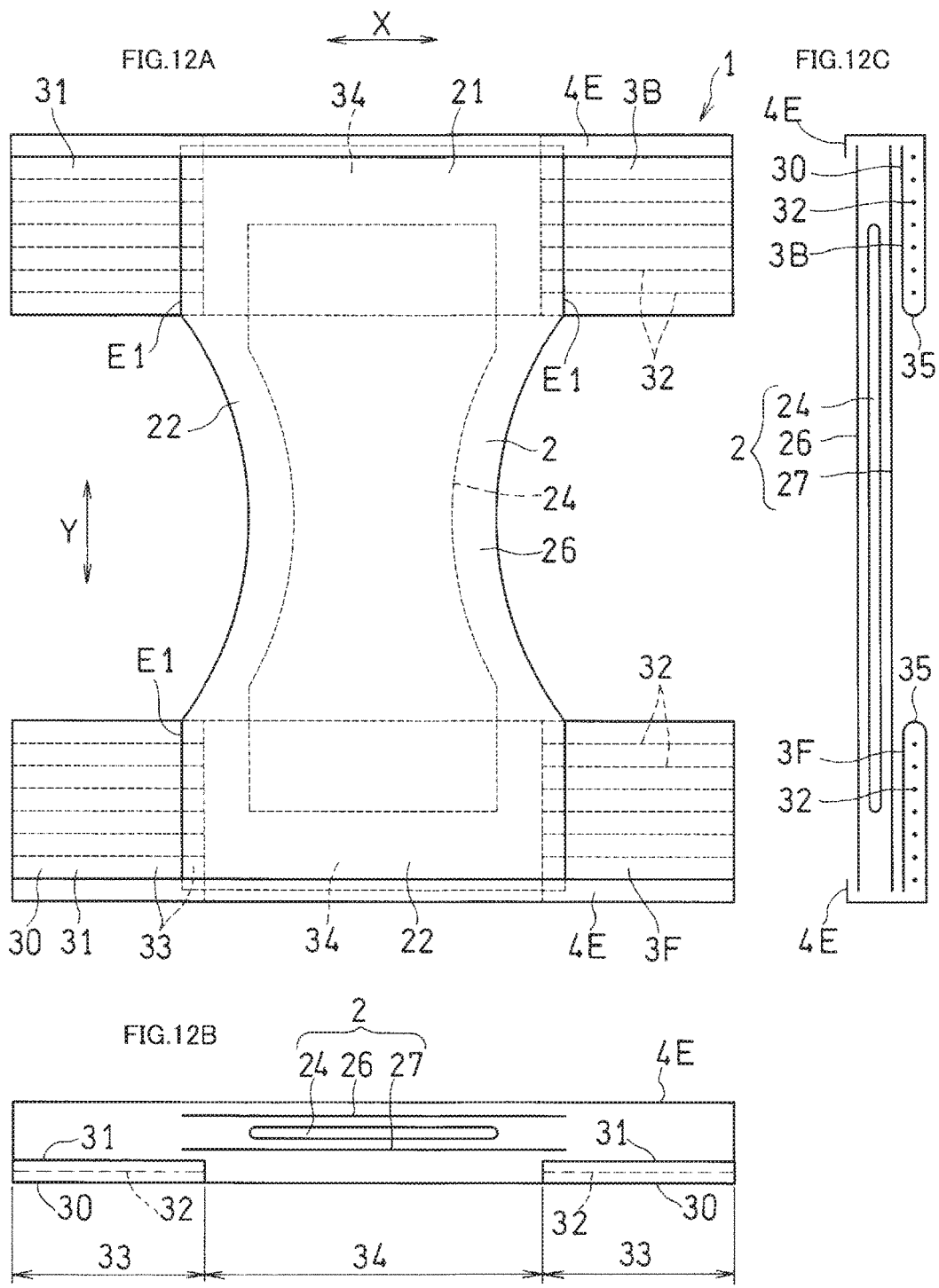
FIG. 12A is a plan view showing still another example of the worn article according to the method of the present invention.
FIG. 12B and FIG. 12C are cross-sectional views showing the still other example.
Figure 13:
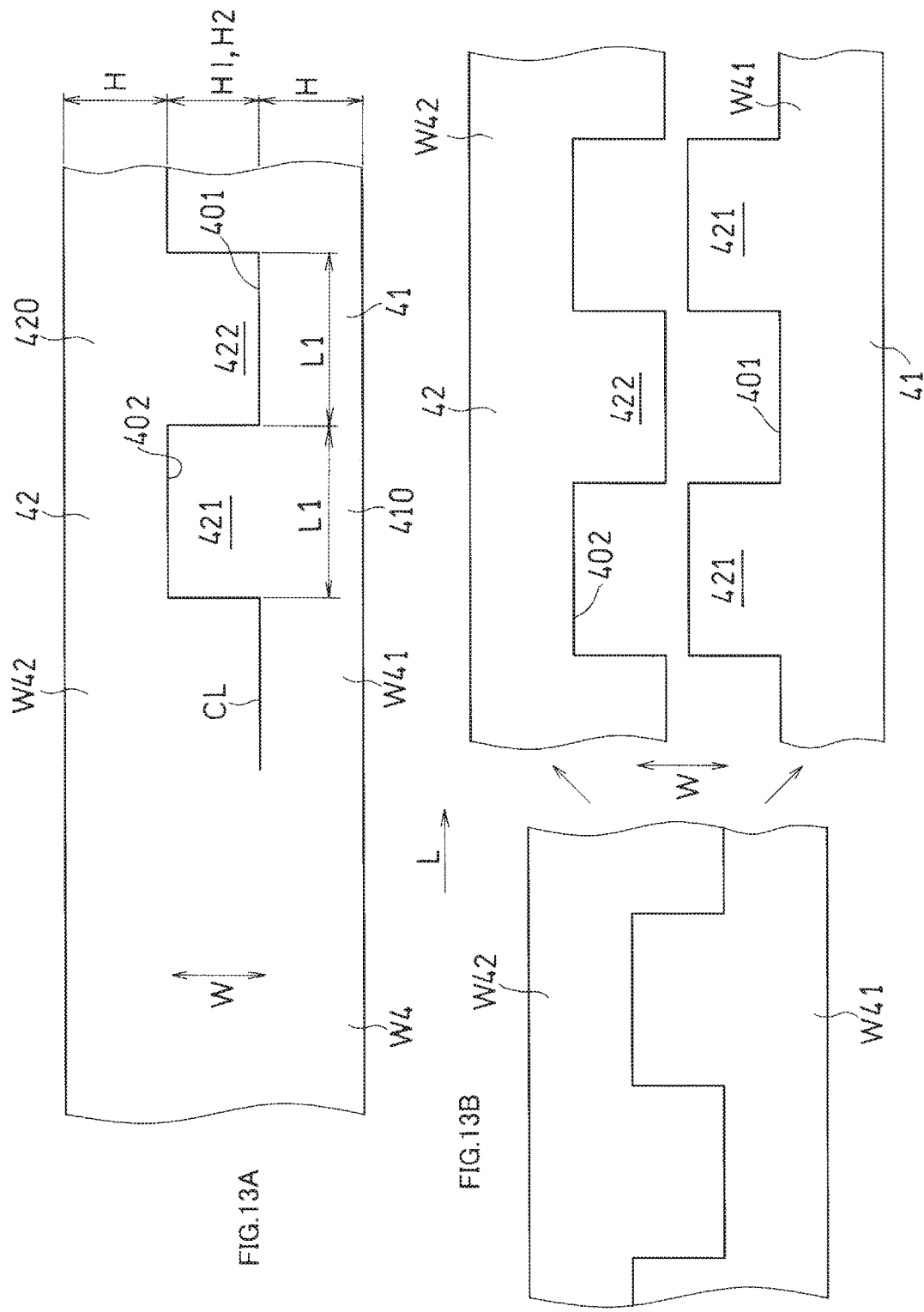
FIG. 13A is a schematic plan view showing the dividing step according to Embodiment 4 of the method of the present invention.
FIG. 13B is a schematic plan view showing the changing step according to this embodiment.
Figure 14:
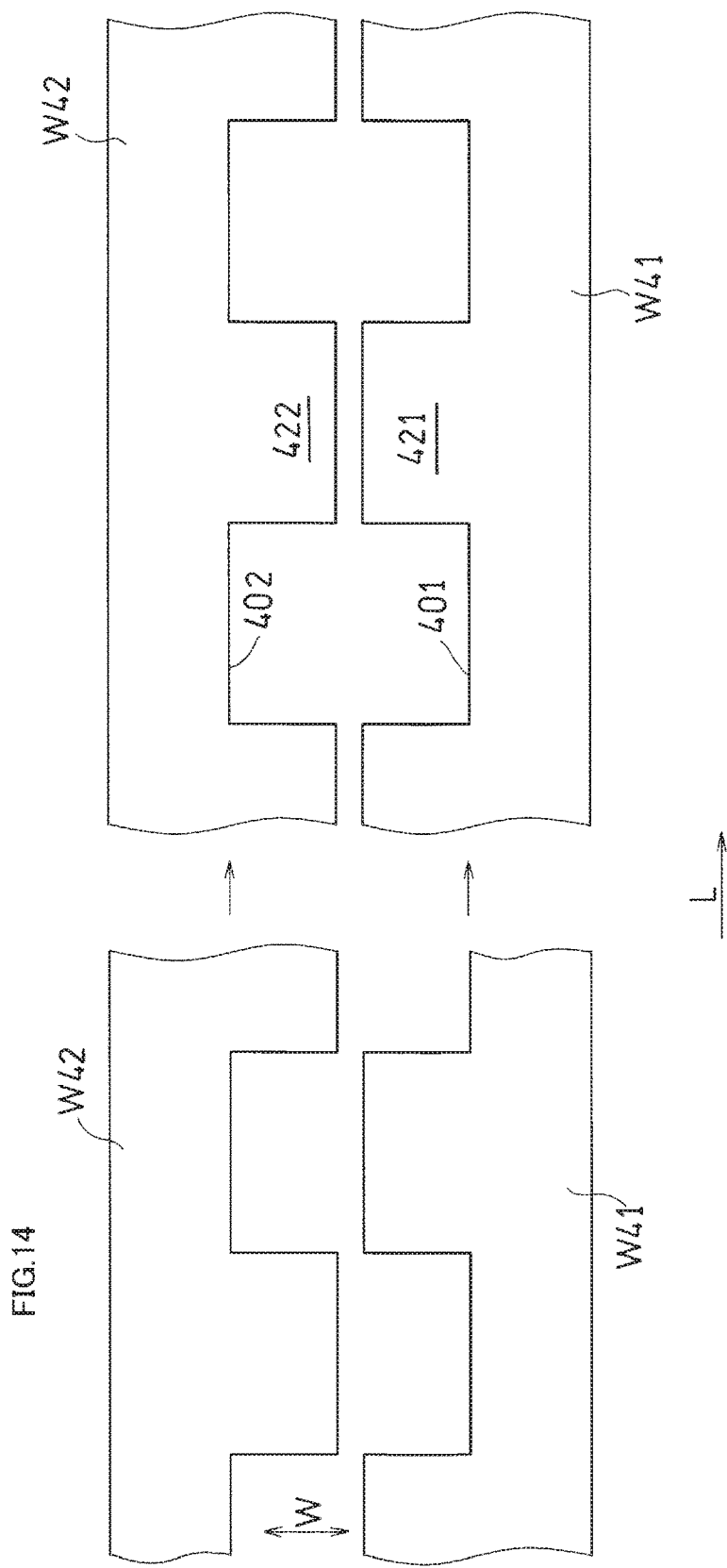
FIG. 14 is a schematic plan view showing the changing step according to Embodiment 4 of the method of the present invention.

In this embodiment, the folding line 4L of FIG. 11 is set at a position protruding from the continuous portion 41, 42 in the width direction W. Therefore, it will be easier to fold the protruding portions 421 and 422 without folding the continuous portion 41, 42.

FIG. 12A to FIG. 15 show Embodiment 4.

As shown in FIG. 12A and FIG. 12C, in this embodiment, the side edge portions 4E of the around-torso members 3F and 3B are folded back continuously along the girth direction X so that portions of the skin-contact surface of the end portions of the absorbent body 2 in the longitudinal direction Y are covered by the side edge portions 4E of the around-torso members 3F and 3B.

In this embodiment, the continuous divided non-woven fabric W4 is severed as shown in FIG. 13A and FIG. 13B.

That is, the dividing step is performed so that the dimension H1 of the first protruding portion 421 in the width direction W is smaller than the dimension H of the continuous portion 41 of the first continuous divided non-woven fabric W41 in the width direction W and so that the dimension H2 of the second protruding portion 422 in the width direction W is smaller than the dimension H of the continuous portion 42 of the second continuous divided non-woven fabric W42 in the width direction W. Therefore, the divided non-woven fabrics W41 and W42 of FIG. 15 may be in a single-layer configuration, where the non-woven fabric is not layered, along the side edge portions 4E of the layered portions 33 and the non-layered portions 34.

Figure 15:
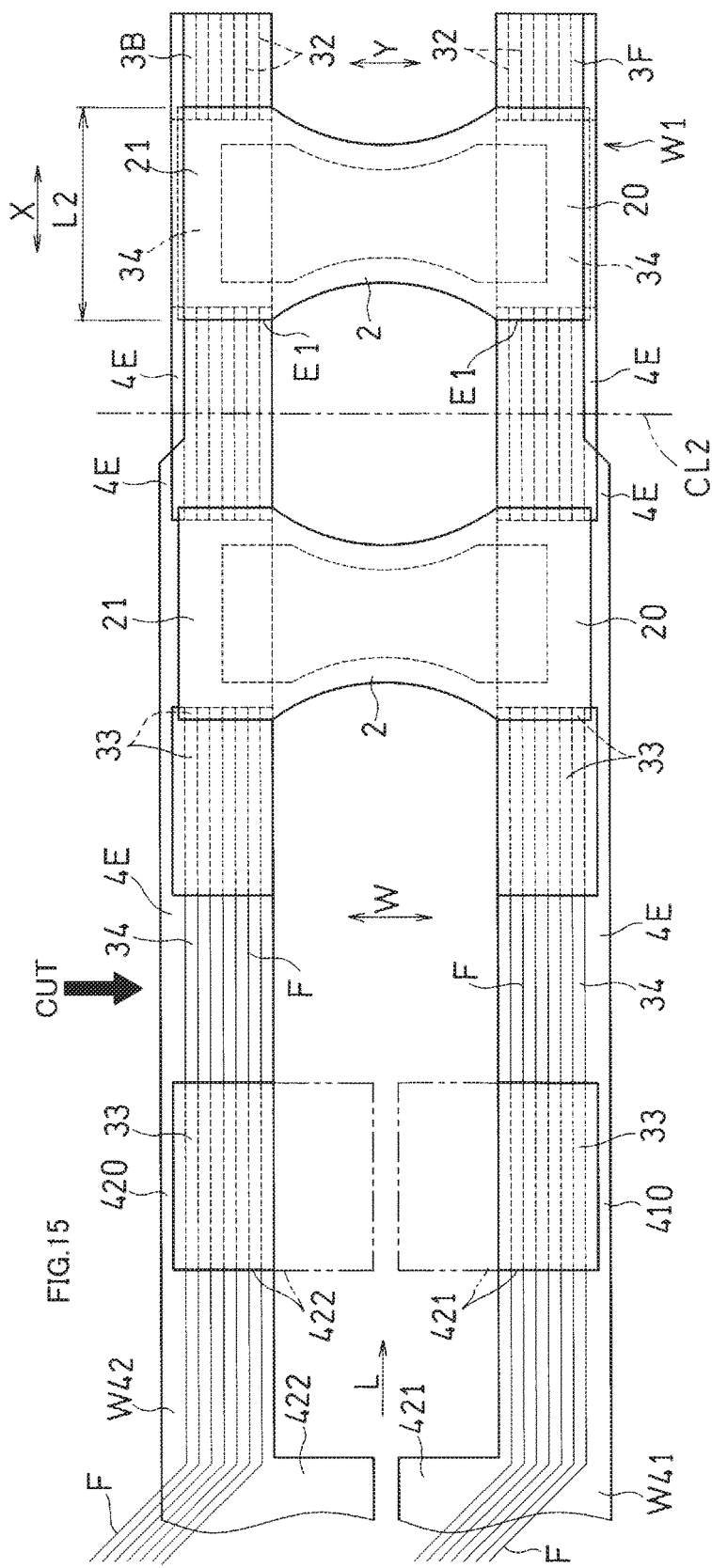
FIG. 15 is a schematic plan view showing the folding step, the fold-back step and the producing step according to Embodiment 4 of the method of the present invention.

The present production method may include a fold-back step shown in FIG. 15 of this embodiment. That is, in the fold-back step, the side edge portions 4E of the divided non-woven fabrics W41 and W42 are folded back continuously along the carrying direction L so that portions of the skin-contact surface of the end portions of the absorbent body 2 in the longitudinal direction Y are covered by the side edge portions 4E.

Now, the present production method includes various embodiments as follows.

For example, in the step of cutting the continuous divided non-woven fabric W4 of FIG. 2A, etc., the first and second protruding portions 421 and 422 do not need to have a perfectly rectangular shape such as an oblong rectangular shape, for example, but may have a rectangle-like shape in which corners at the distal end or the base end of the protruding portions are rounded. The protruding portions may be in a trapezoidal shape or a parallelogram shape. That is, the term "rectangular (rectangle-like, angular) shape" means to include rectangular shapes such as oblong rectangular shapes and trapezoidal shapes, and even those shapes that are approximate to such rectangular shapes.

The heights H1 and 112 of the protruding portions 421 and 422 of FIG. 2A, etc., may be the same as the height H of the base portions 410 and 420. The protruding portions may have the same length L1 or different lengths from each other.

It is preferred that the first protruding portion 421 and the second depressed portion 402 have the same shape and the same size while the second protruding portion 422 and the first depressed portion 401 have the same shape and the same size. Then, there is no need to discard of scrap pieces. However, the protruding portions and the depressed portions may have different shapes or different sizes from each other.

The length L1 of the protruding portions 421 and 422 of FIG. 2A, etc., may be the same as the length L2 of the absorbent body 2 of FIG. 4 in the girth direction X or may be greater than or less than the length L2.

When the continuous elastic member F of FIG. 4 is a cord-like material such as rubber threads, it is preferred that a plurality of threads of the continuous elastic member F are provided for the base portions 410 and 420 or the layered portions 33. On the other hand, when it is a non-continuous elastic member, i.e., a fabric-like material such as a film or a sheet, it is preferred that a sheet of the elastic member is provided for the layered portion 33. In this case, the fabric-like elastic members may be placed intermittently for the base portions 410 and 420 or the protruding portions 421 and 422.

While preferred embodiments have been described above with reference to the drawings, obvious variations and modifications will readily occur to those skilled in the art upon reading the present specification.

For example, a worn article produced by the present production method does not need to have a design pattern, a graphical pattern, or the like, thereon.

Thus, such changes and modifications are deemed to fall within the scope of the present invention, which is defined by the appended claims.

INDUSTRIAL APPLICABILITY

The present invention is applicable to pants-type and diaper-type worn articles.

REFERENCE SIGNS LIST

1: Worn article 2: Absorbent body 20: Front portion (torso portion) 21: Back portion (torso portion) 22: Crotch portion 24: Absorbent core 26: Top sheet 27: Back sheet
3F: Front around-torso member 3B: Rear around-torso member 30: Non-woven fabric 31: Flap 32: Elastic member 33: Layered portion 34: Non-layered portion 35: Bent portion
41: First continuous portion 42: Second continuous portion 4L: Folding line
410, 420: Base portion 421: First protruding portion 422: Second protruding portion
E1: Edge portion F: Continuous elastic member
C1: First severed edge C2: Second severed edge CL: Severing line CL2: Severing line
H, H1, H2: Dimension in width direction
W1: Continuous laminate W4: Continuous non-woven fabric 4E: Side edge portion
W41, W42: Divided non-woven fabric
L: Carrying direction W: Width direction X: Girth direction Y: Longitudinal direction

The invention claimed is:

1. A method for producing a disposable worn article comprising a pair of around-torso members configured to cover a torso of a wearer and extend in a girth direction, and an absorbent body provided so as to bridge between the pair of around-torso members, extending in a longitudinal direction perpendicular to the girth direction, and configured to cover a crotch of the wearer, the method comprising the steps of:

cutting a continuous non-woven fabric, which has a pair of side edge portions extending in a carrying direction, along a wave-shaped cutting line having a predetermined rectangular shape while the continuous non-woven fabric is carried in the carrying direction so as to divide the continuous non-woven fabric into a first continuous divided non-woven fabric and a second continuous divided non-woven fabric, the first continuous divided non-woven fabric having first protruding portions protruding in a width direction perpendicular to the carrying direction from a first continuous portion continuous in the carrying direction, and the first continuous divided non-woven fabric forming one of the pair of around-torso members, the second continuous divided non-woven fabric having second protruding portions protruding in the width direction from a second continuous portion continuous in the carrying direction, and the second continuous divided non-woven fabric forming another one of the pair of around-torso members;

placing at least one elastic member stretchable in the carrying direction at least on the first and second protruding portions of the first and second divided non-woven fabrics, or on base portions of the first continuous portion located at the same positions in the carrying direction as the first protruding portions and on base portions of the second continuous portion located at the same positions in the carrying direction as the second protruding portions;

folding the first and second divided non-woven fabrics so that the elastic member is sandwiched between the base portions and the first protruding portions, adjacent to the base portions, of the first divided non-woven fabric and between the base portions and the second protruding portions, adjacent to the base portions, of the second divided non-woven fabric, and so that layered portions are formed in the first and second divided non-woven fabrics, the layered portions of the first divided non-woven fabric including the first protruding portions laid on the base portions adjacent to the first protruding portions, and the layered portions of the second divided non-woven fabric including the second protruding portions laid on the base portions adjacent to the second protruding portions;

changing a positional relationship between the first and second divided non-woven fabrics so that positions of the base portions of the first continuous divided non-woven fabric in the carrying direction are aligned with positions of the base portions of the second continuous divided non-woven fabric in the carrying direction; and after the changing step, placing the absorbent body so as to bridge between, and to overlap, a non-layered portion of the first continuous divided non-woven fabric and a non-layered portion of the second continuous divided non-woven fabric, the non-layered portion of the first divided non-woven fabric extending between two of the layered portions adjacent to each other in the carrying direction and the non-layered portion of the second divided non-woven fabric extending between two of the layered portions adjacent to each other in the carrying direction, while the first and second continuous divided non-woven fabrics are carried generally in parallel to each other in the carrying direction, thereby producing a continuous laminate.

2. The production method according to claim 1, wherein:
the absorbent body includes a torso portion configured to cover a front torso of the wearer and a torso portion covering a rear torso of the wearer; and
the step of producing the continuous laminate is performed by placing the absorbent body so that two edge portions of the torso portion covering the front torso in the girth direction and two edge portions of the torso portion covering the rear torso in the girth direction respectively overlap portions of two of the layered portions of the first divided non-woven fabric adjacent to each other in the carrying direction and portions of two of the layered portions of the second divided non-woven fabric adjacent to each other in the carrying direction.

3. The production method according to claim 1, wherein:
the dividing step is performed so that a dimension of each of the first protruding portions in the width direction is greater than a dimension of the first continuous portion of the first continuous divided non-woven fabric in the width direction and so that a dimension of each of the second protruding portions in the width direction is greater than a dimension of the second continuous portion of the second continuous divided non-woven fabric in the width direction.

4. The production method according to claim 1, further comprising the step of folding back the side edge portions of the first and second divided non-woven fabrics continuously in the carrying direction so that skin-contact surfaces of end portions of the absorbent body in the longitudinal direction are covered by the side edge portions.

5. The production method according to claim 1, wherein:
the at least one elastic member includes a plurality of elastic members parallel to each other;
the placement step is performed by placing the plurality of elastic members so that the elastic members extend in parallel to each other and continuously in the carrying direction on the first and second continuous portions; and
the method further comprises the step of nullifying tension of some or all of the plurality of elastic members in the non-layered portions of the first and second divided non-woven fabrics so that a shrinkage force of the elastic members is unable to be exerted in the non-layered portions.

6. The production method according to claim 1, wherein:
the step of changing the positional relationship is performed by changing the positional relationship between the first continuous divided non-woven fabric and the second continuous divided non-woven fabric so that the first protruding portions and the second protruding portions oppose each other.

7. The production method according to claim 1, wherein the step of changing the positional relationship comprises:
a first sub-step of changing the positional relationship between the first continuous divided non-woven fabric and the second continuous divided non-woven fabric in the width direction so that the pair of side edge portions are placed between a first severed edge of the first continuous divided non-woven fabric along the severing line and a second severed edge of the second continuous divided non-woven fabric along the severing line and so that the pair of side edges come closer to each other; and
a second sub-step of changing the positional relationship between the first continuous divided non-woven fabric and the second continuous divided non-woven fabric in the carrying direction so that the first protruding portions and the second protruding portions are back to back with each other.

* * * * *